United States Patent
Hu et al.

(10) Patent No.: US 7,629,469 B2
(45) Date of Patent: Dec. 8, 2009

(54) INTERMEDIATE FOR THE PREPARATION OF PALIPERIDONE

(75) Inventors: Tsung-Cheng Hu, Sinshih Township, Tainan County (TW); Hsiao-ping Fang, Yongkang (TW); Hong-Tsung Huang, Taixi Shiang (TW)

(73) Assignee: Scinopharm Taiwan, Ltd., Tainan County (TW)

( * ) Notice: Subject to any disclaimer, the term of this patent is extended or adjusted under 35 U.S.C. 154(b) by 0 days.

(21) Appl. No.: 12/355,141

(22) Filed: Jan. 16, 2009

(65) Prior Publication Data

US 2009/0182150 A1     Jul. 16, 2009

Related U.S. Application Data

(60) Provisional application No. 61/011,309, filed on Jan. 16, 2008.

(51) Int. Cl.
*C07D 405/12* (2006.01)
(52) U.S. Cl. .................... 546/284.4; 546/199; 544/282; 548/241
(58) Field of Classification Search ............. 546/284.4, 546/199; 544/282; 548/241
See application file for complete search history.

(56) References Cited

U.S. PATENT DOCUMENTS

| 5,158,952 | A | 10/1992 | Janssen et al. |
| 2007/0260061 | A1 | 11/2007 | Vreysen et al. |

*Primary Examiner*—Bernard Dentz
*Assistant Examiner*—David E Gallis
(74) *Attorney, Agent, or Firm*—Cohen, Pontani, Lieberman & Pavane LLP

(57) ABSTRACT

A new compound of formula (IV)

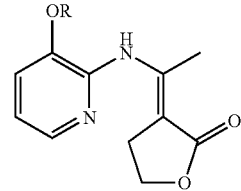

R represents a protecting group which is removable by hydrogenation, and use thereof as an intermediate for preparing paliperidone.

24 Claims, 2 Drawing Sheets

INTERMEDIATE FOR THE PREPARATION OF PALIPERIDONE

RELATED APPLICATIONS

This application claims priority from U.S. Provisional Patent Application Ser. No. 61/011,309 which was filed on Jan. 16, 2008. The content of U.S. Provisional Patent Application Ser. No. 61/011,309 is incorporated herein in its entirety.

BACKGROUND OF THE INVENTION

1. Field of the Invention

The present application relates to a class of new intermediates for producing paliperidone, process of making these new intermediates, and process of making paliperidone.

2. Description of the Related Art

Previously known processes for producing paliperidone have low yields and produce large amounts of HCl gas as a by-product. In U.S. Pat. No. 5,158,952 (its European counterpart is EP0368388), a process is disclosed wherein 2-amino-3-benzyloxypyridine (I') was reacted with 1.7 mole equivalents 2-acetyl-4-butyrolactone in the presence of 5.5 mole equivalents phosphoryl chloride in toluene. The reaction mixture was stirred for 5 hours at 90° C. Another 1.7 mole equivalents of 2-acetyl-4-butyrolactone were then added and the stirring was continued for 30 minutes at 90° C. The solution was allowed to stand overnight at 90° C. The whole was poured into crushed ice and treated with an ammonium hydroxide solution 25%. The product was extracted with trichloromethane. The extract was dried, filtered and evaporated. The residue was purified by column chromatography over silica gel using a mixture of trichloromethane and methanol (98:2 by volume) as eluent. The pure fractions were collected and the eluent was evaporated. The residue was stirred in 2-propanol. The product was filtered off, washed with a mixture of 2-propanol and 1,1'-oxybisethane and dried at 50° C., yielding 20.5 mole equivalents (Yield: 62.3%) of 3-(2-chloroethyl)-2-methyl-9-(phenylmethoxy)-4H-pyrido[1,2-a]pyrimidin-4-one; mp. 141.1° C. See the scheme shown below.

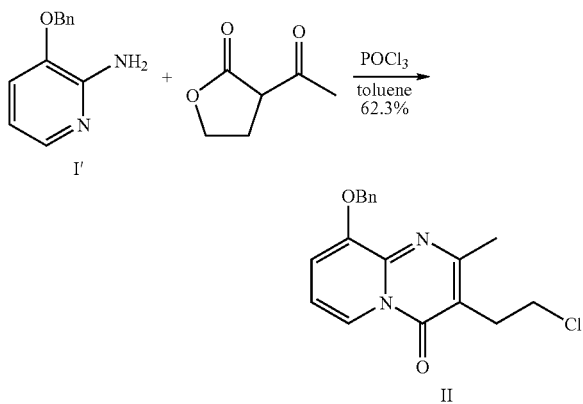

The yield of this condensation reaction is low, and the higher amounts of lactone (about 3.4 mole equivalents) and POCl₃ (about 5.5 mole equivalents) are needed to facilitate this reaction. In addition, POCl₃ releases lots of HCl gas during decomposition. Furthermore, the reaction mixture containing the intermediate II needs to be purified by column chromatography to remove the unreacted 2-amino-3-benzyloxypyridine (I') before further conversion to paliperidone.

Therefore, there is still need for a process of making paliperidone that is easy to operate, incurs low cost, and/or produces a high yield of product.

SUMMARY OF THE INVENTION

In accordance with the first embodiment of the present invention, a new compound of formula IV as shown below is provided:

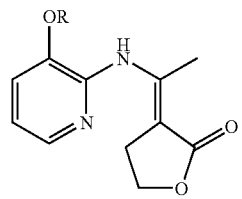

IV wherein R represents a protecting group which is removable by hydrogenation, such as benzyl, allyl, 4-methoxybenzyl, 2,6-dimethylbenzyl, 3,4-dichlorobenzyl, and 4-(dimethylamino)-carbonylbenzyl.

Preferably, the protecting group R is benzyl (Bn). When R is Bn, the chemical name of the above compound of formula IV is 1-(3-benzyloxy-pyridine-2-ylamino)-eth-(E)-ylidene-dihydro-furano-2-one. It can be used as an intermediate for making paliperdione.

In accordance with the second embodiment of the present invention, a process of making the above compound of formula IV is provided. The process comprises: 1) reacting a compound of formula (I):

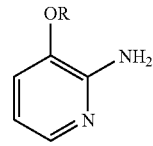

I with 2-acetyl-4-butyrolactone in the presence an effective amount of catalyst to synthesize the compound of formula (IV); and 2) isolating the compound of formula (IV) from the reaction mixture of step 1). Preferably, the reaction is conducted in the presence of a solvent. R in formula (I) represents a protecting group which is removable by hydrogenation, such as benzyl, allyl, 4-methoxybenzyl, 2,6-dimethylbenzyl, 3,4-dichlorobenzyl, and 4-(dimethylamino)-carbonylbenzyl.

The solvent can be selected from the group consisting of toluene, xylene, chlorobenzene, and combinations thereof. Preferably, the solvent is toluene. The catalyst can be selected from the group consisting of p-toluenesulfonic acid, HCl, H₂SO₄, benensulfonic acid, and combinations thereof. Preferably, the catalyst is p-toluenesulfonic acid.

Preferably, the water formed in the above reaction is removed. As a preferred embodiment, the process in accordance with the present invention comprises a step of azeotropic removal of water at reflux temperature after the step of reacting the compound of formula (I) with 2-acetyl-4-butyrolactone. The amount of 2-acetyl-4-butyrolactone is preferable no less than 2.0 mole equivalents, in particular no greater than 3 mole equivalents (relative to the other reactant, i.e., the compound of formula (I)). The removal of water may facilitate the subsequent reaction of the compound of formula (IV) with other reactants. Typically, the water is removed under reduced pressure and a temperature of 50-110° C.

Azeotropic distillation refers to the specific technique of adding another component to generate a new lower-boiling azeotrope. So, the water formed in the reaction can combine with toluene (solvent) to generate the water-toluene azeotrope, the lower boiling point of the azeotrope may assure the complete removal of water. The boiling point of the azeotrope may vary with the proportion of components. The removal of water is preferably conducted under reflux temperature.

Alternatively, other methods may be used to remove the water formed from the above reaction. For example, an inert drying agent may be used to remove the water.

In accordance with the third embodiment of the present invention, a new process of making paliperidone is provided. The process comprises a step of converting a compound of formula IV, as shown above, to paliperidone. Specifically, the process may comprise: 1) reacting the compound of formula (I) with 2-acetyl-4-butyrolactone in the presence of an effective amount of catalyst and preferably, a first solvent, to synthesize the compound of formula (IV); 2) converting the compound of formula (IV) to a compound of formula V:

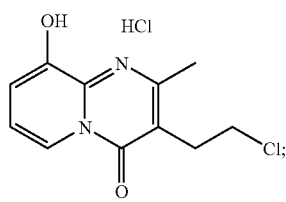

and 3) converting the compound of formula V to paliperidone.

The compound of formula (IV) synthesized in step 1) can be optionally isolated in a solid form from the reaction mixture. Alternatively, the compound of formula (IV) of step 1) without being isolated from the reaction mixture to a solid form can be used directly in step 2). Preferably, as noted above, the water contained in the reaction mixture of step 1) is removed, and the resulting slurry containing the compound of formula (IV) is used in step 2) to prepare the compound of formula (V).

The first solvent may be selected from the group consisting of toluene, xylene chlorobenzene, and combinations thereof. Preferably, the first solvent is toluene. The catalyst can be selected from the group consisting of p-toluenesulfonic acid, HCl, $H_2SO_4$, benensulfonic acid, and combinations thereof. Preferably, the catalyst is p-toluenesulfonic acid.

The above second step of converting the compound of formula (IV) to the compound of formula (V) may comprise the following steps: 2a) reacting the compound of formula (IV) with phosphoryl chloride to obtain a compound of formula V':

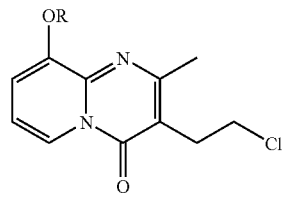

wherein R is the protecting group, as defined above (the protecting group R may be removed by $POCl_3$ from some amount of the product of formula V', i.e., in that case R can be H on the formula V'); and 2b) hydrogenating the compound of formula V' in the presence of hydrochloric acid and a hydrogenation catalyst in a second solvent to provide the compound of formula V.

The second solvent may be selected from the group consisting of methanol (MeOH) and water. Preferably, the second solvent is MeOH. The hydrogenation catalyst contains a metal element selecting from the group consisting of Rh, Pt and Pd. As a preferable embodiment, the hydrogenation catalyst is Pd/C. The temperature is preferably controlled at 20-30° C. during the hydrogenation reaction of step 2). The amount used for phosphoryl chloride is preferable no less than 2 mole equivalents, more particular within the range of 2 to 4 mole equivalents (relative to the reactant 2-amino-3-benzyloxypyridine).

Preferably, compared to the hydrogenation discussed infra for converting a compound of formula (V) to a compound of formula (III), milder condition for the above step 2b) of hydrogenating is used such as, 5% Pd/C (5 wt. %) and at temperature of 20-30° C. (lower concentration and lower temperature). The hydrogenation of the above step 2b) is to remove the protecting group "R".

The compound of formula V) synthesized in the above step 2) can be isolated and briefly purified by agitating, filtering and washing the resulting solids in a suitable solvent, such as acetone, MeOH, EtOH, IPA, ACN, EtOAc/heptane, EtOAc/MTBE, dichloromethane/heptane, and dichloromethane/MTBE, to remove the impurities. Preferably, the solvent is acetone Preferably, the process of the present invention is free of a step of purifying the compound of formula V) by column chromatography. Therefore, the purified compound of formula V can be obtained without conducting column chromatography, which provides a better process for industrial-scale production.

The step of converting the compound of formula V to paliperidone can be carried out in any suitable manner, which, for example, can be a method described in the art. For example, the compound of formula V can be hydrogenated in the presence of Pd/C in alcohol at 45-55° C. to provide a compound of formula III.

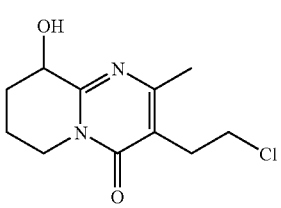

Preferably, compared to the hydrogenating step to remove the protecting group of formula V', supra, stronger conditions are preferred for the hydrogenating of compound of formula V to prepare the compound of formula (III). For example, the hydrogenation here may be conducted in the presence of 10% Pd/C and $H_2$ gas at about 0.15 $Kg/m^2$ and about 50° C.

The compound of formula III can be coupled with 6F-3-4-piperidinyl-1,2-benzisoxazole HCl by N-alkylation reaction to provide paliperidone.

Compared to the prior art, the advantages of the present invention include:

(1) The charged amounts of lactone and $POCl_3$ are reduced (See the previous comments at paragraph 0010 regarding the amount of lactone), which can economize the use of starting materials and lower the formation of pernicious gases (HCl).

(2) The novel compound of formula IV without being isolated from the slurry reaction mixture to a solid state can be directly applied to the subsequent cyclization and hydrogenation reactions to obtain the intermediate V. And the compound of formula V can be briefly purified by agitating in a solvent, such as acetone, to remove the impurities. Therefore, the purified intermediate V can be obtained without conducting column chromatography, which provides a better process for industrial-scale production.

Other objects and features of the present invention will become apparent from the following detailed description considered in conjunction with the accompanying drawings.

DETAILED DESCRIPTION OF THE PRESENTLY PREFERRED EMBODIMENTS

The following embodiments and examples are provided for illustrating, but not for limiting, the present invention.

As shown in the synthetic scheme below, 2-amino-3-benzyloxypyridine (I') is reacted with 2-acetyl-4-butyrolactone in toluene, allowing azeotropic removal of water in the presence of a catalytic amount of p-toluenesulfonic acid at reflux temperature. And then the novel intermediate IV', 1-(3-benzyloxy-pyridine-2-ylamino)-eth-(E)-ylidene-dihydro-furano-2-one, can be obtained. The isolated intermediate IV' or the reaction mixture contained intermediate IV' is reacted with phosphoryl chloride in toluene, and then is hydrogenated in the presence of hydrochloric acid and Pd/C at 20-30° C. to provide the intermediate V. The intermediate V is hydrogenated in the presence of Pd/C in alcohol at 45-55° C. to provide the intermediate III. The intermediate III is coupled with 6F-3-4-piperidinyl-1,2-benzisoxazole HCl by N-alkylation reaction to provide paliperidone.

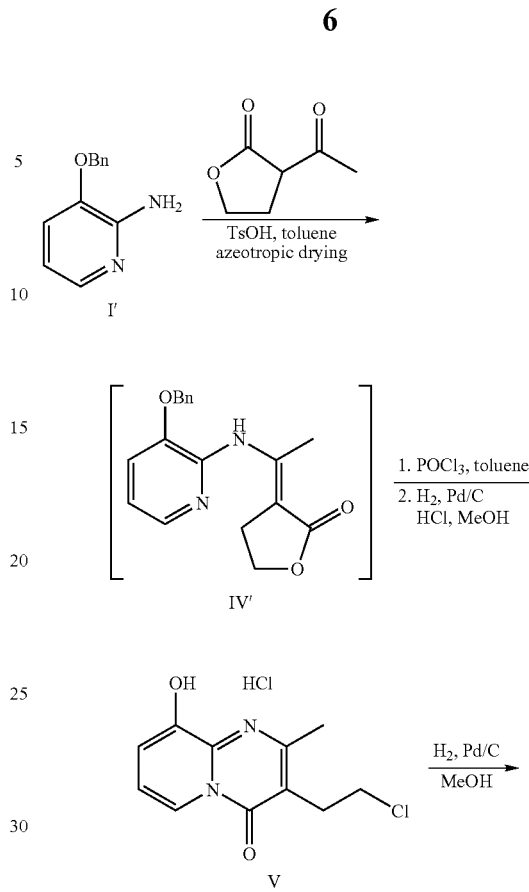

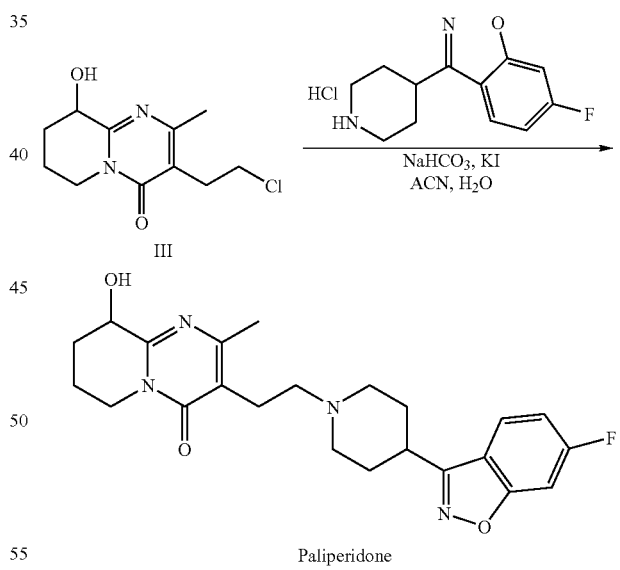

Paliperidone

Figure 1:
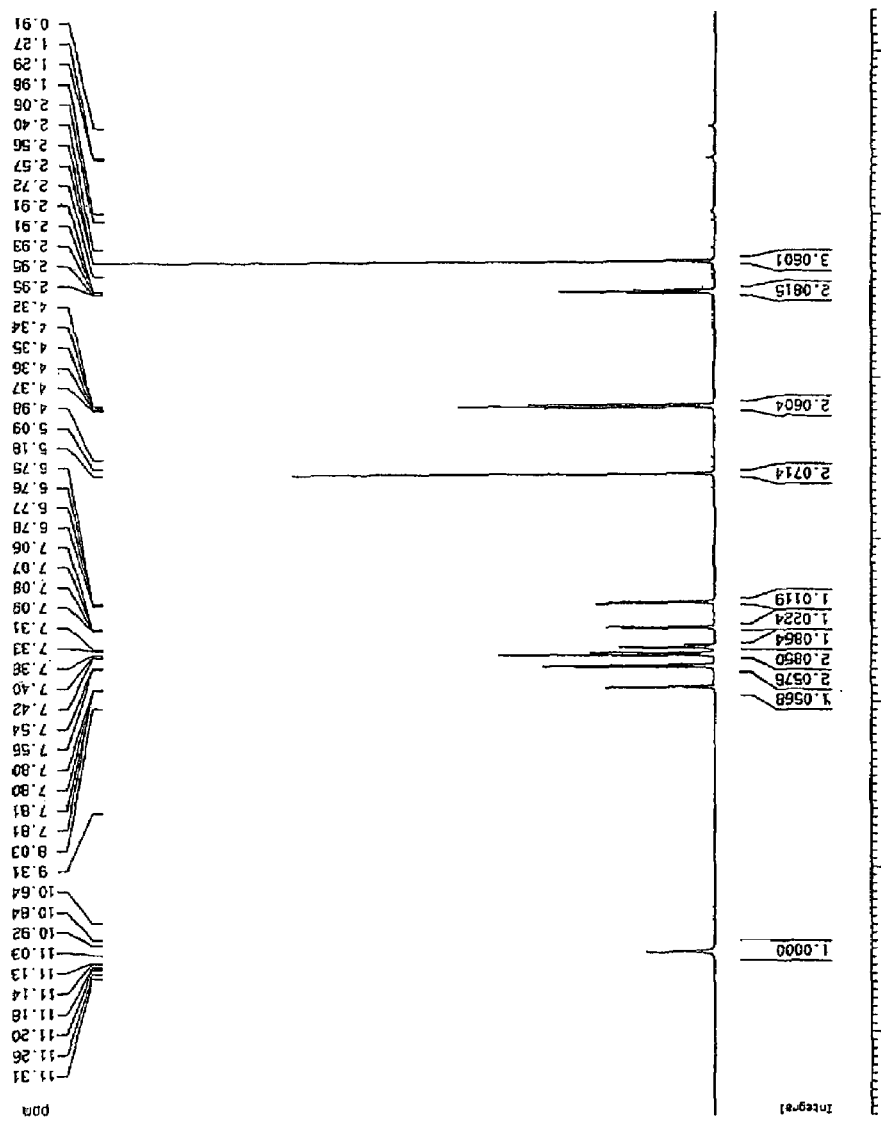
FIG. 1 depicts the $^1$H NMR spectrum of the compound of formula IV' (i.e., the compound of formula IV wherein R is benzyl).

As shown in FIG. 1, the $^1$H NMR (CDCl$_3$) data obtained from the compound of formula IV' is: d 10.92 (s, 1H), 7.81 (d, J=4.0 Hz, 1H), 7.55 (m, 2H), 7.40 (m, 2H), 7.32 (m, 1H), 7.08 (dd, J=8.0, 4.0 Hz, 1H), 6.77 (dd, J=8.0, 4.0 Hz, 1H), 5.09 (s, 2H), 4.35 (t, J=8.0 Hz, 2H), 2.93 (t, J=8.0 Hz, 2H), 2.56 (s, 3H).

Figure 2:
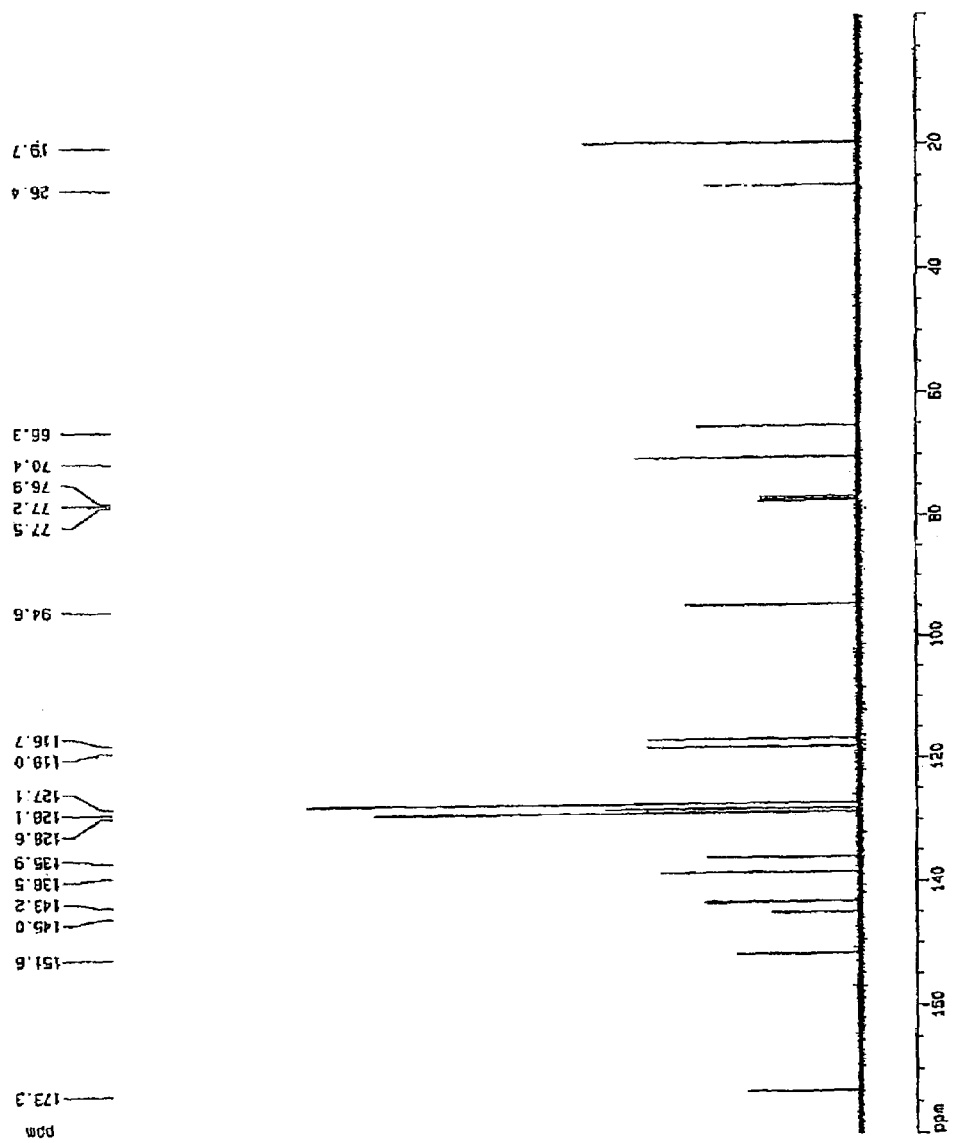
FIG. 2 depicts the $^{13}$C NMR spectrum of the compound of formula IV'.

As shown in FIG. 2, the $^{13}$C NMR (CDCl$_3$) data obtained from the compound of formula IV' is: d 173.3 (C), 151.6 (C), 145.0 (C), 143.2 (C), 138.5 (CH), 135.9 (C), 128.6 (2CH), 128.1 (CH), 127.1 (2CH), 118.0 (CH), 116.7 (CH), 94.6 (C), 70.4 (CH$_2$), 65.3 (CH$_2$), 26.4 (CH$_2$), 19.7 (CH$_3$).

EXAMPLES

Example 1

Step 1a. Enamine Formation

To a suitable reactor is charged with 2-amino-3-benzyloxy-pyridine (the compound of formula I' (160 g, 1 eq.), 2-acetyl-4-butyrolactone (205 g, 2 equivalents), p-toluenesulfonic acid (76.2 g, 0.5 mole equivalent) and toluene (1.6 L, 10 vols). The slurry is allowed to azeotropically dry under reflux temperature.

Example 2

Step 1b. Cyclization

To the resulting mixture of example 1 is added phosphoryl chloride (245 g, 2 eq) and agitated for several hours. After the reaction is completed, the reaction mixture is worked up with water (1.6 L, 10 vols) and allowed to agitate for a while, followed by phase separation. To the organic layer is washed with HCl aqueous solution (800 mL, 5 vols). To the combined aq. layer is added dichloromethane (800 mL 5 vols) and neutralized with NaOH aqueous solution. The collected aqueous layer is extracted with dichloromethane. The combined organic layer is swapped by methanol (1.28 L, 8 vols).

Example 3

Step 1c. Hydrogenation and Salt Formation

To the resulting solution of example 2 is added 5% Pd/C (8 g, 5 wt. %) and concentrated HCl aqueous solution (92 g, 1 mole equivalent), the slurry is hydrogenated at 20-30° C. After the reaction is completed, the solid is filtered and rinsed with methanol (160 mL, 1 vol). To the filtrate is swapped with acetone (800 mL, 5 vols) and agitated for a while. The resulting solid is filtrated and washed with acetone, followed by drying under reduced pressure to provide the compound of formula (V) (147.8 g).

Example 4

Step 2 Hydrogenation

To a suitable reactor is charged with the compound of formula (V, 60 g, 1 eq), 10% Pd/C (6-13g) and methanol (480 mL, 8 vols). The slurry is heated to 45-55° C. and agitated under H$_2$ gas at about 0.15 Kg/m$^2$ for not less than 5 hours. After the reaction is completed, the solid is filtered and rinsed with methanol (120 mL, 2 vols). The filtrated is swapped with water (120 mL, 2 vols) and ethylacetate (180 mL, 3 vols). The resulting mixture is neutralized with saturated sodium carbonate aqueous solution. The slurry is agitated for a while and then filtered and washed with ethylacetate (300 mL 5 vols). The filtrate is settled for phase separation. To the aq. layer is washed with ethylacetate. The combined organic layer is distilled and then filtered. The filtrate is distilled and then N-heptanes (600 mL, 10 vols) is added. The slurry is cooled down and then the solid is filtered and washed with heptanes. The wet cake is dried under reduced pressure to afford the compound of formula III (38.8 g).

Example 5

Step 3 Coupling

To a suitable reactor is charged the compound of formula III (60 g, 1 eq), 6F-3-4-Piperidinyl-1,2-Benzisoxazole HCl (63.4 g, 1.05 eq), sodium bicarbonate (51.4 g, 2.5 eq), potassium iodide (4.8 g, 0.12 eq), water (60 mL, 1 vol) and acetonitrile (540 mL, 9 vol). The slurry is heated to reflux and agitated for several hours. After the reaction is completed, the resulting solids are filtered and washed with water. The wet cake is dried under reduced pressure to provide paliperidone (90.4 g).

The invention is not limited by the embodiments described above which are presented as examples only but can be modified in various ways within the scope of protection defined by the appended patent claims.

We claim:

1. A compound of formula (IV)

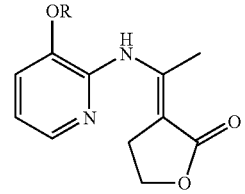

wherein R represents a protecting group which is removable by hydrogenation.

2. The compound of claim 1 wherein the protecting group is selected from the group consisting of benzyl, allyl, 4-methoxybenzyl, 2,6-dimethylbenzyl, 3,4-dichlorobenzyl, and 4-(dimethylamino)-carbonylbenzyl.

3. The compound of claim 1 wherein the protecting group is benzyl.

4. A process for preparing paliperidone, comprising converting a compound of formula (IV):

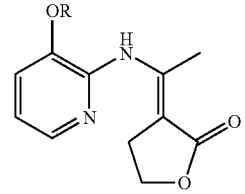

to the paliperidone, wherein R represents a protecting group which is removable by hydrogenation.

5. The process of claim 4 wherein the compound of formula (IV) is synthesized by reacting a compound of formula (I):

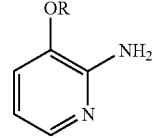

with 2-acetyl-4-butyrolactone in the presence an effective amount of catalyst.

6. The process of claim 5 wherein the reaction between the compound of formula (I) and 2-acetyl-4-butyrolactone is conducted in the presence of a first solvent.

7. The process of claim 6 wherein the first solvent is selected from the group consisting of toluene, xylene, chlorobenzene, and combinations thereof.

8. The process of claim 6 wherein the first solvent is toluene.

9. The process of claim 5 wherein the catalyst is selected from the group consisting of hydrochloric acid (HCl), sulfuric acid ($H_2SO_4$), benzenesulfonic acid, p-toluenesulfonic acid, and combinations thereof.

10. The process of claim 5 wherein the catalyst is p-toluenesulfonic acid.

11. The process of claim 5 wherein process is free of a step to isolate the synthesized compound of formula (IV) from the reaction mixture to a solid form.

12. The process of claim 4 where the step of converting the compound of formula (IV) to the paliperidone comprises: 1) converting the compound of formula (IV) to a compound of formula (V):

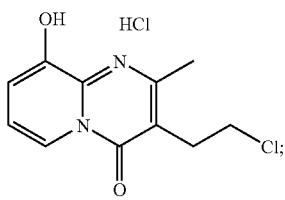

V and 2) converting the compound of formula (V) to paliperidone.

13. The process of claim 12 wherein the step of converting the compound of formula (IV) to the compound of formula (V) comprises: a) reacting the compound of formula (IV) with phosphoryl chloride to obtain a compound of formula (V'):

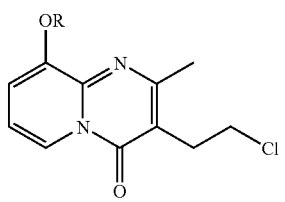

V' wherein R represents a protecting group which is removable by hydrogenation; and b) hydrogenating the compound of formula (V') in the presence of hydrochloric acid and a hydrogenation catalyst in a second solvent to provide the compound of formula (V).

14. The process of claim 13 wherein the second solvent is selected from the group consisting of methanol and water.

15. The process of claim 13 wherein the second solvent is methanol.

16. The process of claim 13 wherein the hydrogenation catalyst contains a metal element selected from the group consisting of Rh, Pt, Pd, and combinations thereof.

17. The process of claim 13 wherein the hydrogenation catalyst is Pd/C.

18. The process of claim 13 wherein the amount of phosphoryl chloride is in the range of 2 to 4 mole equivalents relative to the amount of the compound of formula (IV).

19. The process of claim 13 wherein the process is free of a step of purifying the compound of formula (V) by column chromatography.

20. A process for preparing a compound of formula (IV):

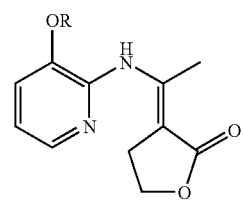

IV comprising a step of reacting a compound of formula (I):

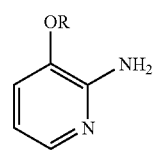

I with 2-acetyl-4-butyrolactone in the presence an effective amount of catalyst; wherein R represents a protecting group which is removable by hydrogenation 21. The process of claim 20 wherein the reaction is conducted in the presence of a solvent.

22. The process of claim 21 wherein the solvent is selected from the group consisting of toluene, xylene, chlorobenzene, and combinations thereof.

23. The process of claim 21 the catalyst is selected from the group consisting of hydrochloric acid (HCl), sulfuric acid ($H_2SO_4$), benzenesulfonic acid, p-toluenesulfonic acid, and combinations thereof.

24. A process for preparing paliperidone, comprising 1) reacting a compound of formula (I'):

with 2-acetyl-4-butyrolactone in the presence an effective amount of p-toluenesulfonic acid to provide a compound of formula (IV'):
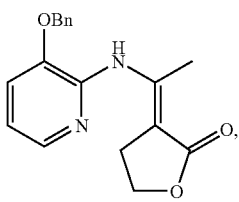
2) converting the compound of formula (IV') to a compound of formula (V):
and 3) converting the compound of formula (V) to paliperidone.
* * * * *